(12) United States Patent
Ci

(10) Patent No.: US 10,701,963 B2
(45) Date of Patent: Jul. 7, 2020

(54) NUTRITIONAL COMPOSITION FOR MOISTURIZING LUNG AND METHOD FOR PREPARING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 292 days.

(21) Appl. No.: 15/958,935

(22) Filed: Apr. 20, 2018

(65) Prior Publication Data

US 2019/0159498 A1    May 30, 2019

(30) Foreign Application Priority Data

Nov. 30, 2017   (CN) .......................... 2017 1 12401726

(51) Int. Cl.

| | | |
|---|---|---|
| *A23L 33/105* | (2016.01) | |
| *A61K 36/8945* | (2006.01) | |
| *A61K 36/8967* | (2006.01) | |
| *A61K 36/752* | (2006.01) | |
| *A61K 36/899* | (2006.01) | |

(52) U.S. Cl.
CPC .......... *A23L 33/105* (2016.08); *A61K 36/752* (2013.01); *A61K 36/899* (2013.01); *A61K 36/8945* (2013.01); *A61K 36/8967* (2013.01); *A23V 2002/00* (2013.01); *A23V 2200/314* (2013.01); *A23V 2250/21* (2013.01); *A23V 2300/10* (2013.01); *A23V 2300/16* (2013.01)

(58) Field of Classification Search
CPC .. A61K 2300/00; A61K 36/076; A61K 36/48; A61K 36/62; A61K 36/725; A61K 36/8994; A23V 2002/00; A23V 2250/21; A23V 2300/10; A23V 2200/324; A23V 2300/16; A23V 2200/30; A23V 2200/32; A23V 2300/14; A23L 33/105; A23L 11/05; A23L 19/09; A23L 19/10; A23L 31/00; A23L 7/143; A23L 7/17; A23P 10/25

See application file for complete search history.

(56) References Cited

U.S. PATENT DOCUMENTS

2015/0037389 A1*  2/2015  Ragot .................... A61K 36/74
                                                        424/439

* cited by examiner

*Primary Examiner* — Aaron J Kosar
(74) *Attorney, Agent, or Firm* — Cantor Colburn LLP

(57) ABSTRACT

The present application discloses a nutritional composition for moisturizing lung. The nutritional composition includes the following components of raw materials in parts by weight: rice 55-90, wheat 7-25, Chinese yam 3-15, lily 2-9, *polygonatum odoratum* 0.2-1, and citron 0.1-1. The present disclosure, in view of the lung's characteristics of being not resistant to cold or heat, and susceptible to pathogen, complies with the lung's physiological function characteristics to regulate, and provides the prescription with nourishing yin and moisturizing lung, and resolving phlegm and relieving cough as a starting point, is suitable to cooperate with staple foods for long-term consumption and easily accepted by people due to the good taste, and can achieve certain efficacies of replenishing and restoring lung qi.

20 Claims, 1 Drawing Sheet

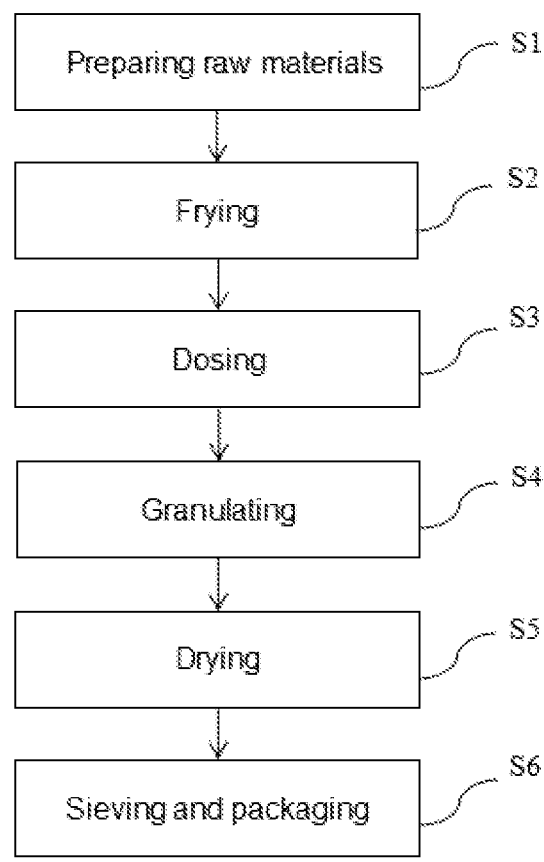

NUTRITIONAL COMPOSITION FOR MOISTURIZING LUNG AND METHOD FOR PREPARING THE SAME

TECHNICAL FIELD

The present disclosure belongs to the technical field of food processing, and particularly relates to a nutritional composition for moisturizing lung and a method for preparing the same.

BACKGROUND

Fast-pace and high-intensity work, deliberate competition, ceaseless stress, long-term metal strain and so on are heavy burdens for people in modern society. Moreover, when reaching middle ages, people's physiological functions decline, and many people develop syndromes belonging to kidney deficiency in traditional Chinese medical science, such as pains in waist and back, tinnitus, dizziness, pale facial complexion, declined physical functions, cold extremities, mental fatigue, and sleeping disorder, all of which further form invisible metal stress, and seriously affect the life quality. Traditional Chinese medical science holds that the lung governs qi (vital energy), which generally means that the lung governs both breathing air and all the qi of the body. "The lung stores the spirit, has the attribute of gold, and governs all the qi of the body" ("Zhou Shi Yi Xue Cong Shu•Zang Fu Biao Ben Yao Shi (Collections of Writings on Medicine of Mr. Zhou•Medication Based on Conditions of the Zang-fu Organs, Symptom and Root, Cold and Heat, Deficiency)"). All the qi of the human body is governed by the lung, therefore, "all the qi pertains to the lung" ("Su Wen•Wu Zang Sheng Cheng Lun (Basic Questions•Discourse on the Creation and Formation of the Five Zang-Organs)"), "the lung governs all the qi of the body" ("Yi Men Fa Lv•Ming Xiong Zhong Da Qi Zhi Fa (Laws for Physicians•Methods for Understanding Air in Chest)"). The lung governing qi includes two aspects, i.e. governing the breathing air and governing all the qi of the body.

The lung is a place where qi in vivo and in vitro exchange. The lung breathes in clear qi in the nature, and breathes out foul qi in the body, realizing the exchange of air in vivo and in vitro. By continuously breathing out the foul air and breathing in the clear air, and getting rid of the stale and taking in the fresh, the generation of qi is promoted, and the up and down, and in and out movements of qi are regulated, so that the metabolism of the human body is ensured to carry out normally. In the traditional medicines of more than 5000 years of the Chinese nation, some natural plant drugs indeed have curative effects in repairing and improving the lung functions. The invaluable experience, handed down from generation to generation, upon continuous application, development, and perfection of medical experts and health experts of successive dynasties, has become a type of unique natural plant drug (Chinese herbal medicine for moisturizing the lung) with the nourishing and strengthening efficacies. However, every medicine has its side effect, and long-term consumption of a lot of Chinese herbal medicine inevitably will cause damages to other aspects of the body.

On the basis of dietotherapy (homology between medicine and food) regimen of the traditional Chinese medical science, more and more dieticians reasonably match food materials with the homology between medicine and food, and achieve the object of nourishing yin and moisturizing the lung through the function of channel tropism of the food materials' four natures and five tastes.

Currently, similar health-care products with the function of moisturizing the lung are already available in the market, but in most cases, the matching of different foods is chaotic, does not follow the pharmacology, and has relatively bad taste.

SUMMARY

A main object of the present disclosure is to provide a health-care food for nourishing yin and moisturizing the lung.

In order to achieve the above object, according to one aspect of the present disclosure, a nutritional composition for moisturizing lung is provided.

The nutritional composition for moisturizing lung according to the present disclosure includes the following components of raw materials in parts by weight: rice 55-90, wheat 7-25, Chinese yam 3-15, lily 2-9, *polygonatum odoratum* 0.2-1, and citron 0.1-1.

Furthermore, the nutritional composition for moisturizing lung includes the following components of raw materials in parts by weight: rice 60-80, wheat 10-20, Chinese yam 6-11, lily 4-7, *polygonatum odoratum* 0.4-0.7, and citron 0.3-0.6.

Furthermore, the nutritional composition for moisturizing lung includes the following components of raw materials in parts by weight: rice 70, wheat 15, Chinese yam 9, lily 5, *polygonatum odoratum* 0.5, and citron 0.5.

Furthermore, the nutritional composition for moisturizing lung further includes a Chinese herbal medicine extract of 1-3 parts, wherein the Chinese herbal medicine extract includes the following components of raw materials in parts by weight: ginkgo 10-28, root of balloonflower 8-22, hawthorn 5-16, peach seed 3-10, dried tangerine peel 4-17, cinnamon 0.3-2, kudzu vine root 4-13, and *angelica dahurica* 1-10.

In order to achieve the above object, according to another aspect of the present disclosure, a method for processing a nutritional composition for moisturizing lung is further provided.

The method for processing a nutritional composition for moisturizing lung according to the present disclosure includes the following steps in sequence:

step 1, preparing raw materials: purifying and sorting rice, wheat, Chinese yam, lily, *polygonatum odoratum*, and citron for subsequent use;

step 2, frying: frying respective components of raw materials under a condition of 100-200° C. for 25-120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains;

step 5: drying: drying the mixed rice grains through a microwave dryer, wherein a water content of the material is kept below 12%, and cooling the dried mixed rice grains at a room temperature;

step 6: sieving and packaging: sieving the cooled mixed rice grains, and vacuum-packaging the sieved mixed rice grains.

Furthermore, temperatures of three phases of the double-screw extruder are kept at 60° C., 90-120° C., and 90° C., respectively.

Furthermore, a heating temperature of the microwave dryer is kept at 50-60° C.

Furthermore, in a dosing process of the step 3, a Chinese herbal medicine extract of 1-3 parts is further added, and the Chinese herbal medicine extract includes the following components of raw materials in parts by weight: ginkgo 10-28, root of balloonflower 8-22, hawthorn 5-16, peach seed 3-10, dried tangerine peel 4-17, cinnamon 0.3-2, kudzu vine root 4-13, and *angelica dahurica* 1-10.

Furthermore, the Chinese herbal medicine extract is prepared through the following method:

drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract.

Furthermore, in a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa.

The present disclosure, in view of the lung's characteristics of being not resistant to cold or heat, and susceptible to pathogen, complies with the lung's physiological function characteristics to regulate, and provides the prescription with nourishing yin and moisturizing lung, and resolving phlegm and relieving cough as a starting point, is suitable to cooperate with staple foods for long-term consumption, is easily accepted by people due to the good taste, and can achieve certain efficacies of replenishing and restoring lung qi.

BRIEF DESCRIPTION OF DRAWINGS

The FIGURE, constituting a portion of the present application, is used for further understanding of the present disclosure, so as to make it more obvious other features, objects, and advantages of the present application. Exemplary examples of the present disclosure, drawing, and description thereof are used to explain the present disclosure, rather than improperly limiting the present disclosure. In the FIGURE, FIG. 1 is a flow chart of a technology for processing a nutritional composition of examples of the present disclosure.

DETAILED DESCRIPTION OF EMBODIMENTS

In order to make a person skilled in the art better understand solutions of the present invention, below technical solutions of the examples of the present invention will be described clearly and completely in conjunction with the FIGURE of the examples of the present invention. Apparently, some but not all of examples of the present invention are described. Based on the examples of the present invention, all the other examples, which a person ordinarily skilled in the art obtains without paying inventive effort, fall within the scope of protection of the present invention.

Besides, the term "include (comprise)" and any variants thereof are intended to cover non-exclusive containing, for example, a product including a series of raw materials or a method including a series of steps is not necessarily limited to listing those raw materials or steps, but may include other steps or raw materials which are not clearly listed or inherent to the method or product.

It should be indicated that examples of the present invention and features in the examples can be combined with each other without conflict. The present invention will be described in detail with reference to the FIGURES in conjunction with the examples.

A main object of the present disclosure is to provide a health-care food for nourishing yin and moisturizing lung.

In one aspect, the present disclosure provides a nutritional composition having such function, including the following components of raw materials in parts by weight: rice 55-90, wheat 7-25, Chinese yam 3-15, lily 2-9, *polygonatum odoratum* 0.2-1, and citron 0.1-1.

Rice: the traditional Chinese medical science holds that rice is sweet in taste and mild in nature, exerts the curative effect through the spleen, stomach, and lung channels, has the efficacies of nourishing the middle energizer and supplementing qi, tonifying the spleen and nourishing the stomach, replenishing the essence and improving the memory, harmonizing the internal organs, promoting the blood circulation, improving the hearing and eyesight, eliminating annoyance, quenching thirst, and curing diarrhea, and it is believed that taking more rice can "strengthen the body and improve the look".

Wheat: wheat, cold in nature and sweet in taste, exerts the curative effect through the heart, spleen, and kidney channels, nourishes the heart and relieves restlessness, tonifies the spleen and invigorates the kidney, and eliminates heat and quenches thirst.

Chinese yam: Chinese yam, sweet in taste and mild in nature, exerts the curative effect through the spleen, lung, and kidney channels, supplements qi, nourishes yin, tonifies the spleen and lung, tonifies kidney to strengthen essence, and is used for treatment of reduced spleen-deficiency appetite, loose stool with indigested grains, lung-deficiency cough, gonobolia, frequent urination, and yin-deficiency diabetes.

Lily: lily, sweet in taste and cold in nature, exerts the curative effect through the heart and lung channels, nourishes yin, moisturizes the lungs, clears away the heart fire, and calms the nerves, and is used for treatment of yin-deficiency dry coughing, overstrained cough and hemoptysis, fidgeting due to deficiency and palpitation, insomnia and dreaminess, and trance.

*Polygonatum odoratum: polygonatum odoratum*, sweet in taste and mild in nature, exerts the curative effect through the lung and stomach channels, nourishes yin and moisturizes the lung, generates the body fluid and nourishes the stomach, and is used for treatment of yin-deficiency dry coughing, polydipsia and dry mouth, and internal heat and consumptive thirst.

Citron: citron, acrid, bitter, and sour in taste and warm in nature, exerts the curative effect through the liver, spleen, and lung channels, soothes the liver and regulates qi, regulates the middle energizer, and eliminates phlegm, and is used for treatment of qi-stagnation in the liver and stomach, distending pain in chest and hypochondrium, abdominal distention and fullness, vomiting and eructation, excessive phlegm and cough.

The nutritional composition of the present disclosure achieves a perfect combination of dietotherapy and medical therapy by scientifically matching the principle of medicinal and edible dual purposes in combination with reasonable traditional Chinese medicines, reflecting the traditional preparing characteristics of the Chinese herbal medicine and providing the prescription based on the theory of the traditional Chinese medical science, and further enriching the purposes of the nutritional composition, i.e. regulation, balancing, supplementation, and keeping fit. It has the main efficacy of moisturizing the lung. The above composition can be taken as daily regulation diet.

On the basis of the above examples, the nutritional composition further includes a Chinese herbal medicine extract of 1-3 parts, wherein the Chinese herbal medicine extract includes the following components of raw materials in parts by weight: ginkgo 10-28, root of balloonflower 8-22, hawthorn 5-16, peach seed 3-10, dried tangerine peel 4-17, cinnamon 0.3-2, kudzu vine root 4-13, and *angelica dahurica* 1-10.

Hawthorn: hawthorn, sour and sweet in taste and slightly warm in nature, exerts the curative effect through the spleen, stomach, and liver channels, promotes the digestion, invigorates the stomach, promotes the circulation of qi and dissipates the blood stasis, resolves turbidity and reduces lipid, and is used for treatment of meat-type food accumulation, stomach distention abdominal distention, diarrhea stomachache, blood stasis amenorrhea, postpartum stagnation, pricking in heart and abdomen, chest obstruction and cardiac pain, hernia pain, and hyperlipemia.

Peach seed: peach seed, bitter and sweet in taste and mild in nature, exerts the curative effect through the heart, liver, and large intestine channels, removes blood stasis, relaxes bowel, relieves cough and asthma, and is used for treatment of amenorrhea and algomenorrhea, agglomeration in abdominal cavity, pulmonary abscess and intestinal carbuncle, traumatic injury, constipation due to intestinal dryness, and cough asthma.

Ginkgo: ginkgo, sweet, bitter, and astringent in taste, mild in nature, and slightly toxic, exerts the curative effect through the lung channel, astringes the lungs, relieves asthma, promotes astriction, and arrests leucorrhoea, and is used for treatment of asthma with abundant phlegm, leucorrhoea, gonorrhea, and enuresis and frequent urination.

Root of balloonflower: root of balloonflower, bitter and acrid in taste and mild in nature, exerts the curative effect through the lung channel, ventilates the lung, relieves sore throat, eliminates the phlegm, expels the pus, and is used for the treatment of cough with abundance of phlegm, chest oppression, sore throat and hoarse voice, and pulmonary abscess and pyemesis.

Dried tangerine peel: dried tangerine peel, acrid and bitter in taste, mild in nature, exerts the curative effect through the lung and spleen channels, regulates qi and the middle energizer, eliminates dampness and phlegm, and is used for treatment of cough with abundance of phlegm, indigestion, liquor damage, nausea and oppression in the abdomen.

Cinnamon: cinnamon, astringent and sweet in taste and extremely hot in nature, exerts the curative effect through the kidney, spleen, heart, and liver channels, has the efficacy of tonifying fire and helping yang, guiding fire to origin, eliminating cold to stop pain, and warming the meridians, and is used for treatment of impotence and uterine cold, waist and knee crymodynia, kidney deficiency asthma, yang deficiency with upper manifestation, dizziness and hot eyes, heart and abdomen crymodynia, deficiency-cold vomiting and diarrhea, cold abdominal colic stomachache, dysmenorrhea and amenorrhea.

Kudzu vine root: kudzu vine root, sweet and acrid in taste and cold in nature, exerts the curative effect through the lung and stomach channels, relieves the muscles and skin and allay fever, promotes eruption, generates the body fluid and quenches thirst, invigorates yang and cures diarrhea, and is used for treatment of syndrome of fever, sever back pain, measles without adequate eruption, thirst caused by fever, yin-deficiency diabetes, heat diarrhea, and spleen-deficiency diarrhea.

*Angelica dahurica*: angelica dahurica, acrid in taste and warm in nature, exerts the curative effect through the lung, spleen, and stomach channels, relieves exterior syndrome by diaphoresis, dispels wind to alleviate pain, frees nasal orifices, dries dampness and arrests leucorrhoea, relieves swelling and discharges pus, dispels wind and arrests itching, and is used for treatment of common cold due to wind-cold, headache, toothache, rheumatic arthralgia, nasosinusitis, leucorrhoea, and carbuncle.

A small amount of the Chinese herbal medicine extract is added to the nutritional composition for improving the function of moisturizing the lung of the nutritional composition. In the Chinese herbal medicine extract, the root of balloonflower ventilates the lung and eliminates the phlegm, the ginkgo astringes the lungs and promotes astriction; the hawthorn promotes the digestion, promotes the circulation of qi and dissipates the blood stasis, the peach seed removes blood stasis, the dried tangerine peel regulates qi and the middle energizer, the cinnamon helps yang and eliminates cold; the kudzu vine root can promote eruption and generate the body fluid; the *angelica dahurica* relieves exterior syndrome by diaphoresis. The efficacies of moisturizing the lung and dissipating the blood stasis, resolving phlegm and stopping coughing are achieved by using various drugs in combination. Moreover, the usage amount of the Chinese herbal medicine extract is relatively small, then it will not destroy the nutritional structure of the original nutritional composition, and will not produce an undesirable taste.

As shown in FIG. 1, a method for preparing the nutritional composition includes the following steps in sequence:

step 1, preparing raw materials: purifying and sorting rice, wheat, Chinese yam, lily, *polygonatum odoratum*, and citron for subsequent use, wherein the raw materials are strictly checked, and impurities and soils are removed, effectively reducing the remnant of pollutants such as heavy metals and pesticides;

step 2, frying: frying respective components of raw materials under a condition of 100-200° C. for 25-120 min, wherein the temperature should not be too high to make the starchy food produce acrylamide, thus preventing loss of nutrients;

step 3, dosing: grinding the respective fried raw materials, then mixing and stirring evenly the respective ground raw materials according to proportions to obtain a rice powder, wherein the proportions of the respective raw materials are based on the prescription of the nutritional composition of the present disclosure, and in the dosing process, a Chinese herbal medicine extract of 1-3 parts is further added, and the Chinese herbal medicine extract includes the following components of raw materials in parts by weight: ginkgo 10-28, root of balloonflower 8-22, hawthorn 5-16, peach seed 3-10, dried tangerine peel 4-17, cinnamon 0.3-2, kudzu vine root 4-13, and *angelica dahurica* 1-10. Specifically, the Chinese herbal medicine extract can be prepared through the following method: drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract. In a process of preparing the Chinese herbal medicine extract, a vacuum dryer is used for drying, a temperature parameter is 75° C.-80° C., and a vacuum degree is between a negative pressure of 0.08 MPa and a negative pressure of 0.1 MPa;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90-120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50-60° C.;

step 6: sieving and packaging: sieving the cooled mixed rice grains, and vacuum-packaging the sieved mixed rice grains, wherein the appearance and homogeneity of product particles can be improved by sieving, and in practical operation, after completing the packaging, a product name, a product lot number, specification, net weight, date of manufacture, name of position, and person in charge are recorded and tagged, and a delivery receipt is filled in, then the product is transferred to an intermediate station.

Example 1

A nutritional composition for moisturizing lung includes the following components of raw materials in parts by weight: rice 55-90, wheat 7-25, Chinese yam 3-15, lily 2-9, polygonatum odoratum 0.2-1, and citron 0.1-1.

A preparation method is as follows:

step 1, preparing raw materials: purifying and sorting rice, wheat, Chinese yam, lily, polygonatum odoratum, and citron for subsequent use;

step 2, frying: frying respective components of raw materials under a condition of 100° C. for 120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50° C.;

step 6: sieving and packaging: sieving the cooled mixed rice grains, and vacuum-packaging the sieved mixed rice grains.

Example 2

A nutritional composition for moisturizing lung includes the following components of raw materials in parts by weight: rice 55-90, wheat 7-25, Chinese yam 3-15, lily 2-9, polygonatum odoratum 0.2-1, and citron 0.1-1.

A preparation method is as follows:

step 1, preparing raw materials: purifying and sorting rice, wheat, Chinese yam, lily, polygonatum odoratum, and citron for subsequent use;

step 2, frying: frying respective components of raw materials under a condition of 200° C. for 25 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 60° C.;

step 6: sieving and packaging: sieving the cooled mixed rice grains, and vacuum-packaging the sieved mixed rice grains.

Example 3

A nutritional composition for moisturizing lung includes the following components of raw materials in parts by weight: rice 60-80, wheat 10-20, Chinese yam 6-11, lily 4-7, polygonatum odoratum 0.4-0.7, and citron 0.3-0.6.

A preparation method is as follows:

step 1, preparing raw materials: purifying and sorting rice, wheat, Chinese yam, lily, polygonatum odoratum, and citron for subsequent use;

step 2, frying: frying respective components of raw materials under a condition of 120° C. for 80 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 100° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 58° C.;

step 6: sieving and packaging: sieving the cooled mixed rice grains, and vacuum-packaging the sieved mixed rice grains.

Example 4

A nutritional composition for moisturizing lung includes the following components of raw materials in parts by weight: rice 60-80, wheat 10-20, Chinese yam 6-11, lily 4-7, polygonatum odoratum 0.4-0.7, and citron 0.3-0.6.

A preparation method is as follows:

step 1, preparing raw materials: purifying and sorting rice, wheat, Chinese yam, lily, polygonatum odoratum, and citron for subsequent use;

step 2, frying: frying respective components of raw materials under a condition of 130° C. for 60 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 105° C., and 90° C., respectively;

step 5: drying: drying the mixed rice grains through a microwave dryer, wherein a water content of the material is kept below 12%, cooling the dried mixed rice grains at a room temperature, wherein a heating temperature of the microwave dryer is kept at 53° C.;

step 6: sieving and packaging: sieving the cooled mixed rice grains, and vacuum-packaging the sieved mixed rice grains.

Example 5

A nutritional composition for moisturizing lung includes the following components of raw materials in parts by weight: rice 70, wheat 15, Chinese yam 9, lily 5, polygonatum odoratum 0.5, and citron 0.5.

A preparation method is as follows:

step 1, preparing raw materials: purifying and sorting rice, wheat, Chinese yam, lily, *polygonatum odoratum*, and citron for subsequent use;

step 2, frying: frying respective components of raw materials under a condition of 150° C. for 40 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 6

A nutritional composition for moisturizing lung includes the following components of raw materials in parts by weight: rice 70, wheat 15, Chinese yam 9, lily 5, *polygonatum odoratum* 0.5, citron 0.5, and a Chinese herbal medicine extract 1. The Chinese herbal medicine extract includes the following components of raw materials in parts by weight: ginkgo 10-28, root of balloonflower 8-22, hawthorn 5-16, peach seed 3-10, dried tangerine peel 4-17, cinnamon 0.3-2, kudzu vine root 4-13, and *angelica dahurica* 1-10. The Chinese herbal medicine extract is prepared through the following method: drying and grinding respective raw materials into a medicinal powder, subjecting the medicinal powder to ultrasonic extraction, centrifugation, and concentration with an ethanol solution of 65% in volume percentage to obtain the Chinese herbal medicine extract. In a process of preparing the Chinese herbal medicine extract, a vacuum dryer is used for drying, a temperature parameter is 75° C., and a vacuum degree is a negative pressure of 0.08 MPa.

A method for preparing the nutritional composition is as follows:

step 1, preparing raw materials: purifying and sorting rice, wheat, Chinese yam, lily, *polygonatum odoratum*, and citron for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 7

A nutritional composition for moisturizing lung includes the following components of raw materials in parts by weight: rice 70, wheat 15, Chinese yam 9, lily 5, *polygonatum odoratum* 0.5, citron 0.5, and a Chinese herbal medicine extract 1. The Chinese herbal medicine extract includes the following components of raw materials in parts by weight: ginkgo 28, root of balloonflower 22, hawthorn 16, peach seed 10, dried tangerine peel 17, cinnamon 2, kudzu vine root 13, and *angelica dahurica* 10. The Chinese herbal medicine extract is prepared through the following method: drying and grinding respective raw materials into a medicinal powder, subjecting the medicinal powder to ultrasonic extraction, centrifugation, and concentration with an ethanol solution of 40% in volume percentage to obtain the Chinese herbal medicine extract. In a process of preparing the Chinese herbal medicine extract, a vacuum dryer is used for drying, a temperature parameter is 80° C., and a vacuum degree is a negative pressure of 0.1 MPa.

A method for preparing the nutritional composition is as follows:

step 1, preparing raw materials: purifying and sorting rice, wheat, Chinese yam, lily, *polygonatum odoratum*, and citron for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Experiment Example 1: Sensory Evaluation of Eating Quality

Evaluating method: scoring is made in comparison with reference samples according to the odor, appearance structure, palatability, taste, and cold rice texture of the rice, and an overall score is sum of respective items. Scoring rules are shown in Table 1. Products used for the sensory evaluation of this experiment example are staple foods, numbered as products 1 to 7, obtained by mixing the nutritional compositions for moisturizing lung obtained in Examples 1 to 7 of the present disclosure with rice, respectively, a mixing ratio of rice to the nutritional composition for moisturizing lung being 4:1. Statistical results of the evaluation scores corresponding to the products 1 to 7 are shown in Table 2.

An overall score of less than 50 indicates "very bad", 51-60 "bad", 61-70 "ordinary", 71-80 "relatively good", 81-90 "good", and more than 90 "excellent".

Uncovered matters such as specific operation steps, preparation work, evaluator determination, sample approval, instrument, and appliance should comply with GB/T 15682-2008 Inspection of Grain and Oils—Method for Sensory Evaluation of Paddy or Rice Cooking and Eating Quality.

TABLE 1

Scoring Rules for Sensory Evaluation of Steamed Rice

| First-grade Index Score | Second-grade Index Score | Description of specific properties: score |
|---|---|---|
| Odor 20 | Authenticity and Intensity 20 | Having unique aroma of steamed rice, rich in fragrance: 18~20 |
| | | Having unique aroma of steamed rice, delicate in fragrance of steamed rice: 15~17 |
| | | Having unique aroma of steamed rice, but not obvious in fragrance: 12~14 |
| | | Having no fragrance, but without undesirable odor: 7~12 |
| | | Having an undesirable odor: 0~6 |
| Appearance Structure 20 | Color 7 | Bright in color: 6~7 |
| | | Normal in color: 4~5 |
| | | Dull in color: 0~3 |
| | Gloss 8 | Having obvious gloss: 7~8 |
| | | Slightly glossy: 5~6 |
| | | Having no gloss: 0~4 |
| | Integrity of Steamed Rice Grain 5 | Compact steamed rice structure, good integrity of steamed rice grain: 4~5 |
| | | Most of the steamed rice having a compact and complete structure: 3 |
| | | Some steamed rice grains explode: 0~2 |
| Palatability 30 | Viscosity 10 | Smooth, Viscous, not sticky to teeth: 8~10 |
| | | Viscous, basically not sticky to teeth: 6~7 |
| | | Viscous, sticky to teeth; or not viscous: 0~5 |
| | Elasticity 10 | Chewy: 8~10 |
| | | Slightly shewy: 6~7 |
| | | Loose, hard, feeling foreign matters present: 0~5 |
| | Hardness 10 | Neither too hard nor too soft: 8~10 |
| | | Slightly hard or slightly soft: 6~7 |
| | | Very hard or very soft: 0~5 |
| Taste 25 | Authenticity and Persistence 25 | Having relatively strong fragrance and sweet taste when chewed: 22~25 |
| | | Having light fragrance and sweet taste when chewed: 18~21 |
| | | Having no fragrance or sweet taste when chewed, but without undesirable odor: 16~17 |
| | | Having no fragrance or sweet taste when chewed, but having an undesirable odor: 0~15 |
| Cold Steamed Rice Texture 5 | Agglomeration, Viscoelasticity, and Hardness 5 | Relatively loose, relatively good in viscoelasticity, moderate in hardness: 4~5 |
| | | Agglomerated, slightly bad in viscoelasticity, slightly hardened: 2~3 |
| | | Hardened, bad in viscoelasticity, and more rigid: 0~1 |

TABLE 2

Statistical Table of Results of Evaluation Scores of Respective Products

| Group | Overall Score/Score | Evaluation Result |
|---|---|---|
| Product 1 | 92 | Excellent |
| Product 2 | 94 | Excellent |
| Product 3 | 94 | Excellent |
| Product 4 | 93 | Excellent |
| Product 5 | 90 | Excellent |
| Product 6 | 87 | Good |
| Product 7 | 89 | Good |

It can be seen from the above test results that all the sensory evaluation results made by respective sensory evaluators on the nutritional compositions for moisturizing lung prepared in Examples 1 to 7 in conjunction with rice are "excellent" and "good". It is indicated that the products of the present disclosure have relatively excellent performances in odor, appearance structure, palatability, taste, and cold rice texture.

Experiment Example 2: Test of Relieving Cough

1. Animal: SPF mice, half females and half males, with a body weight of 20±2 g.

2. Supply: the nutritional compositions prepared in Examples 1-7 of the present disclosure, rice, and strong aqua ammonia.

3. Statistical method

Experiment results are expressed by x±SD, normal distribution data is checked with t, and skewed distribution is checked with a sum of ranks.

4. Experiment method 80 mice were selected, 40 females and 40 males, and randomly divided into 8 groups according to sex and body weight, i.e. one control group, and seven test groups. Except the control group, the mice in the other groups were administrated by gavage with the nutritional compositions of Examples 1 to 7 according to the dosage of 0.2 g/kg each time, three times a day, continuously for 14 d, and the mice in the control group were fed with an equal amount of rice. The administration by gavage was continued for 14 d, and 1 h after the last time of administration by gavage, the mice were placed in an inverted beaker of 500 ml, and a cotton ball of 50 mg with absorbtion of 0.3 ml strong aqua ammonia was placed in the beaker. Cough incubation periods and coughing times of the mice within 3 minutes were observed and recorded for the mice in each group (typical cough refers to contraction of abdominal muscle of the mice, while opening mouth wide, accompanied with cough sound). Analysis and statistics of the experiment data was made with variance. Experiment results are shown in Table 3.

TABLE 3

Influence of Nutritional Composition for Moisturizing Lung on Mice's Cough Caused by Aqua Ammonia

| Group | Amount | Incubation Period/S | Coughing Times of the Mice within 3 min/Times |
|---|---|---|---|
| Control Group | 10 | 49 ± 6 | 48 ± 7 |
| Example 1 | 10 | 95 ± 8 ** | 33 ± 6 ** |
| Example 2 | 10 | 97 ± 6 ** | 29 ± 8 ** |
| Example 3 | 10 | 88 ± 12 ** | 20 ± 4 ** |
| Example 4 | 10 | 85 ± 9 ** | 25 ± 6 ** |
| Example 5 | 10 | 99 ± 7 ** | 20 ± 5 ** |
| Example 6 | 10 | 104 ± 13 ** | 19 ± 6 ** |
| Example 7 | 10 | 108 ± 15 ** | 17 ± 5 ** |

Compared with the control group,
** $p < 0.01$.

As can be seen from Table 3, compared with the control group, the cough incubation periods corresponding to the nutritional compositions for moisturizing lung in Examples 1 to 7 have extremely significant differences ($p<0.01$), compared with the control group, the coughing times within 3 minutes corresponding to the nutritional compositions for moisturizing lung in Examples 1 to 7 have extremely significant differences ($p<0.01$), indicating that the nutritional compositions of the present disclosure can obviously prolong the cough incubation period of the mice induced by aqua ammonia and reduce the coughing times, and showing that the present nutritional compositions have obvious functions of moisturizing the lung and relieving the cough.

Besides, as can be seen from comparison of Examples 1 to 5, with the same raw materials and the only difference in compatible proportion, among the five examples, Example 5 has the longest cough incubation period and the least coughing times within 3 minutes, indicating that the nutritional composition of Example 5 has the most obvious effect of relieving the cough, and that it is an optimal example. As can be seen from comparison of Examples 5 to 7, compared with Example 5, the Chinese herbal medicine extract is added to Examples 6 and 7, the cough incubation periods of Examples 6 and 7 are longer than Example 5, and the coughing times within 3 minutes of Examples 6 and 7 are less than Example 5, indicating that the addition of the Chinese herbal medicine extract can further enhance the effect of the nutritional composition in relieving the cough.

The foregoing only describes preferred examples of the present invention and is not intended to limit the present invention. For a person skilled in the art, various modifications and variations may be made to the present invention. Any modifications, equivalent replacements, improvements, etc., made within the spirit and principle of the present invention, should be covered by the scope of protection of the present invention.

What is claimed is:

1. A nutritional composition for moisturizing lung, comprising the following raw material components and proportions thereof, in parts by weight (pbw): rice 55-90 pbw, wheat 7-25 pbw, Chinese yam 3-15 pbw, lily 2-9 pbw, *Polygonatum odoratum* 0.2-1 pbw, and citron 0.1-1 pbw, wherein the composition is a composition prepared by the process comprising the following sequential steps:
   step 1, preparing raw materials: purifying and sorting rice, wheat, Chinese yam, lily, *Polygonatum odoratum*, and citron for subsequent use;
   step 2, frying: frying the prepared raw materials under a condition of 100-200° C. for 25-120 min;
   step 3, dosing: grinding the fried raw materials, then mixing and stirring evenly the ground materials according to the proportions to obtain a rice powder;
   step 4, granulating: extruding the rice powder obtained in step 3 through a double-screw extruder, followed by gelatinization and granulation thereof, to obtain mixed rice grains;
   step 5, drying: drying the mixed rice grains through a microwave dryer, wherein a water content of the material is kept below 12%, and cooling the dried mixed rice grains at room temperature; and
   step 6, sieving and packaging: sieving the cooled mixed rice grains, and optionally vacuum-packaging the sieved mixed rice grains, thereby obtaining the lung-moisturizing nutritional composition.

2. The nutritional composition for moisturizing lung of claim 1, comprising: rice 60-80 pbw, wheat 10-20 pbw, Chinese yam 6-11 pbw, lily 4-7 pbw, *Polygonatum odoratum* 0.4-0.7 pbw, and citron 0.1-1 pbw.

3. The nutritional composition for moisturizing lung of claim 2, further comprising a Chinese herbal medicine extract of 1-3 parts, wherein the Chinese herbal medicine extract comprises the following components of raw materials in parts by weight (pbw): ginkgo 10-28 pbw, root of balloonflower 8-22 pbw, hawthorn 5-16 pbw, peach seed 3-10 pbw, dried tangerine peel 4-17 pbw, cinnamon 0.3-2 pbw, kudzu vine root 4-13 pbw, and *Angelica dahurica* 1-10 pbw.

4. The nutritional composition for moisturizing lung of claim 1, comprising: rice 60-80 pbw, wheat 10-20 pbw, Chinese yam 6-11 pbw, lily 4-7 pbw, *Polygonatum odoratum* 0.4-0.7 pbw, and citron 0.3-0.6 pbw.

5. The nutritional composition for moisturizing lung of claim 4, further comprising a Chinese herbal medicine extract of 1-3 parts, wherein the Chinese herbal medicine extract comprises the following components of raw materials in parts by weight (pbw): ginkgo 10-28 pbw, root of balloonflower 8-22 pbw, hawthorn 5-16 pbw, peach seed 3-10 pbw, dried tangerine peel 4-17 pbw, cinnamon 0.3-2 pbw, kudzu vine root 4-13 pbw, and *Angelica dahurica* 1-10 pbw.

6. The nutritional composition for moisturizing lung of claim 1, further comprising a Chinese herbal medicine extract of 1-3 parts, wherein the Chinese herbal medicine extract comprises the following components of raw materials in parts by weight (pbw): ginkgo 10-28 pbw, root of balloonflower 8-22 pbw, hawthorn 5-16 pbw, peach seed 3-10 pbw, dried tangerine peel 4-17 pbw, cinnamon 0.3-2 pbw, kudzu vine root 4-13 pbw, and *Angelica dahurica* 1-10 pbw.

7. A method for preparing a nutritional composition for moisturizing lung of claim 1, wherein the method comprises the following steps in sequence:
   step 1, preparing raw materials: purifying and sorting rice, wheat, Chinese yam, lily, *Polygonatum odoratum*, and citron for subsequent use;
   step 2, frying: frying the prepared raw materials under a condition of 100-200° C. for 25-120 min;
   step 3, dosing: grinding the fried raw materials, then mixing and stirring evenly the ground materials according to proportions sufficient to obtain a rice powder;
   step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the lung-moisturizing nutritional composition.

8. The method for preparing a nutritional composition for moisturizing lung of claim 7, wherein temperatures of three phases of the double-screw extruder are maintained at 60° C., 90-120° C., and 90° C., respectively.

9. The method for preparing a nutritional composition for moisturizing lung of claim 7, wherein a heating temperature of the microwave dryer is maintained at 50-60° C.

10. The method for preparing a nutritional composition for moisturizing lung of claim 7, wherein in the dosing process of step 3 further comprises adding, in parts by weight of the composition (pbw), a Chinese herbal medicine extract of 1-3 pbw, wherein the Chinese herbal medicine extract comprises the following components of raw materials in parts by weight (pbw): ginkgo 10-28 pbw, root of balloonflower 8-22 pbw, hawthorn 5-16 pbw, peach seed 3-10 pbw, dried tangerine peel 4-17 pbw, cinnamon 0.3-2 pbw, kudzu vine root 4-13 pbw, and *Angelica dahurica* 1-10 pbw.

11. The method for preparing a nutritional composition for moisturizing lung of claim 10, wherein the Chinese herbal medicine extract is prepared by:

drying and grinding the respective component raw materials into a medicinal powder, and subjecting the medicinal powder to ultrasonic extraction, centrifugation, and concentration with an ethanol solution of 40-65% in volume percentage, thereby obtaining the Chinese herbal medicine extract.

12. The method for preparing a nutritional composition for moisturizing lung of claim 11, wherein in the process of preparing the Chinese herbal medicine extract, a vacuum dryer is used for drying, the vacuum dryer providing a temperature of 75° C. to 80° C. and a vacuum negative pressure of from 0.08 MPa to a vacuum negative pressure of 0.1 MPa.

13. A method for preparing a nutritional composition for moisturizing lung of claim 2, wherein the method comprises the following steps in sequence:

step 1, preparing raw materials: purifying and sorting rice, wheat, Chinese yam, lily, *Polygonatum odoratum*, and citron for subsequent use;

step 2, frying: frying the prepared raw materials under a condition of 100-200° C. for 25-120 min;

step 3, dosing: grinding the fried raw materials, then mixing and stirring evenly the ground materials according to proportions sufficient to obtain a rice powder;

step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the lung-moisturizing nutritional composition.

14. The method for preparing a nutritional composition for moisturizing lung of claim 13, wherein temperatures of three phases of the double-screw extruder are maintained at 60° C., 90-120° C., and 90° C., respectively.

15. The method for preparing a nutritional composition for moisturizing lung of claim 13, wherein a heating temperature of the microwave dryer is maintained at 50-60° C.

16. The method for preparing a nutritional composition for moisturizing lung of claim 13, wherein in a dosing process of the step 3, a Chinese herbal medicine extract of 1-3 parts is further added, and the Chinese herbal medicine extract comprises the following components of raw materials in parts by weight: ginkgo 10-28 pbw, root of balloonflower 8-22 pbw, hawthorn 5-16 pbw, peach seed 3-10 pbw, dried tangerine peel 4-17 pbw, cinnamon 0.3-2 pbw, kudzu vine root 4-13 pbw, and *Angelica dahurica* 1-10 pbw.

17. The method for preparing a nutritional composition for moisturizing lung of claim 16, wherein the Chinese herbal medicine extract is prepared by:

drying and grinding the respective component raw materials into a medicinal powder, and subjecting the medicinal powder to ultrasonic extraction, centrifugation, and concentration with an ethanol solution of 40-65% in volume percentage, thereby obtaining the Chinese herbal medicine extract.

18. The method for preparing a nutritional composition for moisturizing lung of claim 17, wherein in the process of preparing the Chinese herbal medicine extract, a vacuum dryer is used for drying, the vacuum dryer providing a temperature of 75° C. to 80° C. and a vacuum negative pressure of from 0.08 MPa to a vacuum negative pressure of 0.1 MPa.

19. A method for preparing a nutritional composition for moisturizing lung of claim 4, wherein the method comprises the following steps in sequence:

step 1, preparing raw materials: purifying and sorting rice, wheat, Chinese yam, lily, *Polygonatum odoratum*, and citron for subsequent use;

step 2, frying: frying the prepared raw materials under a condition of 100-200° C. for 25-120 min;

step 3, dosing: grinding the fried raw materials, then mixing and stirring evenly the ground materials according to proportions sufficient to obtain a rice powder;

step 4, granulating: extruding the rice powder obtained in step 3 through a double-screw extruder, followed by gelatinization and granulation thereof, to obtain mixed rice grains;

step 5, drying: drying the mixed rice grains through a microwave dryer, wherein a water content of the material is kept below 12%, and cooling the dried mixed rice grains at room temperature; and step 6, sieving and packaging: sieving the cooled mixed rice grains, and optionally vacuum-packaging the sieved mixed rice grains, thereby obtaining the lung-moisturizing nutritional composition.

20. The method for preparing a nutritional composition for moisturizing lung of claim 19, wherein temperatures of three phases of the double-screw extruder are maintained at 60° C., 90-120° C., and 90° C., respectively.

* * * * *